США005683995A

United States Patent [19]

Holt et al.

[11] Patent Number: 5,683,995
[45] Date of Patent: Nov. 4, 1997

[54] 17 SUBSTITUTED ACYL-3-CARBOXY 3,5-DIENE STEROIDALS AS α-REDUCTASE INHIBITORS

[75] Inventors: Dennis Alan Holt, Stow, Mass.; Mark Alan Levy, Wayne, Pa.

[73] Assignee: SmithKline Beecham Corporation, Philadelphia, Pa.

[21] Appl. No.: 436,242

[22] PCT Filed: Nov. 18, 1993

[86] PCT No.: PCT/US93/11225

§ 371 Date: Sep. 15, 1995

§ 102(e) Date: Sep. 15, 1995

[87] PCT Pub. No.: WO94/11004

PCT Pub. Date: May 26, 1994

[30] Foreign Application Priority Data

Nov. 18, 1992 [GB] United Kingdom ............... 9224213
Aug. 14, 1993 [GB] United Kingdom ............... 9316954

[51] Int. Cl.[6] .................. A61K 31/56; C07J 3/00; C07J 43/00
[52] U.S. Cl. .................. 514/169; 552/610; 552/548; 540/110
[58] Field of Search ............... 540/94; 552/610; 514/172, 169

[56] References Cited

U.S. PATENT DOCUMENTS

| 4,954,446 | 9/1990 | Holt et al. ............... 435/184 |
| 5,017,568 | 5/1991 | Holt et al. ............... 514/173 |
| 5,032,586 | 7/1991 | Metcalf et al. ............ 514/176 |
| 5,041,433 | 8/1991 | Holt et al. ............... 514/176 |
| 5,137,882 | 8/1992 | Holt et al. ............... 514/182 |
| 5,196,411 | 3/1993 | Rasmusson et al. ........ 514/169 |
| 5,212,166 | 5/1993 | Panzeri et al. ............ 514/176 |

FOREIGN PATENT DOCUMENTS

| 0 343 954 | 11/1989 | European Pat. Off. . |
| 0 465 123 A2 | 1/1992 | European Pat. Off. . |
| 0 567 271 A2 | 10/1993 | European Pat. Off. . |
| WO 93/14106 | 1/1993 | WIPO . |
| WO 93/16097 | 2/1993 | WIPO . |
| WO 93/16098 | 2/1993 | WIPO . |
| WO 93/22333 | 11/1993 | WIPO . |
| WO 94/11385 | 5/1994 | WIPO . |

OTHER PUBLICATIONS

J. Med. Chem. 33, pp. 943–950 (1990).
J. Med. Chem. 33, pp. 937–942 (1990).
Biochemistry, vol. 29, No. 11, pp. 2815–2830 (1990).

*Primary Examiner*—Mark L. Berch
*Assistant Examiner*—Bruck Kifle
*Attorney, Agent, or Firm*—Wayne J. Dustman; Charles M. Kinzig; Edward T. Lentz

[57] ABSTRACT

Invented are 17α and 17β-substituted acyl-3-carboxy-3,5-diene analogues of steroidal synthetic compounds, pharmaceutical compositions containing these compounds, and methods for using these compounds to inhibit steroid 5-α-reductase. Also invented are intermediates and processes used in preparing these compounds.

4 Claims, No Drawings

17 SUBSTITUTED ACYL-3-CARBOXY 3,5-DIENE STEROIDALS AS α-REDUCTASE INHIBITORS

FIELD OF THE INVENTION

The present invention relates to certain novel 17α and 17β substituted acyl-3-carboxy 3,5-diene steroidal compounds, pharmaceutical compositions containing these compounds, and methods for using these compounds to inhibit steroid 5-α-reductase. Also invented are novel intermediates and processes useful in preparing these compounds.

DESCRIPTION OF RELATED ART

The class of steroidal hormones known as androgens is responsible for the physical characteristics that differentiate males from females. Of the several organs that produce androgens, the testes produce these hormones in the greatest amounts. Centers in the brain exert primary control over the level of androgen production. Numerous physical manifestations and disease states result when ineffective control results in excessive androgen hormone production. For example, acne vulgaris, seborrhea, female hirsutism, male pattern baldness and prostate diseases such as benign prostatic hypertropy are correlated with elevated androgen levels. Additionally, the reduction of androgen levels has been shown to have a therapeutic effect on prostate cancer.

Testosterone is the principal androgen secreted by the testes and is the primary androgenic steroid in the plasma of males. It now is known that 5-α-reduced androgens are the active hormones in some tissues such as the prostate and sebaceous gland. Circulating testosterone thus serves as a prohormone for dihydrotestosterone (DHT), its 5-α-reduced analogue, in these tissues but not in others such as muscle and testes. Steroid 5-α-reductase is a Nicotinamide Adenine dinucleotide Phosphate(NADPH)dependent enzyme that converts testosterone to DHT. The importance of this enzyme in male development was dramatically underscored by the discovery of a genetic steroid 5-α-reductase deficiency in male pseudohermaphrodites. Imperato-McGinley, J., et al., (1979), *J. Steroid Biochem.* 11:637–648.

Recognition of the importance of elevated DHT levels in various disease states has stimulated many efforts to synthesize inhibitors of this enzyme. Among the most potent inhibitors identified to date are 3-carboxy-androsta-3,5-diene steroidal derivatives.

A number of 5-α-reductase inhibitors are known in the art. For example,

1. *Bioinorganic Chemistry,* 17, pp. 372–376 (1986), by B. W. Metcalf, et al. describes the inhibition of human steroid 5α reductase (EC 1.3.1.30) by 3 androstene-3-carboxylic acids;

2. *Biochemistry* (1990) Vol. 29, pp. 2815–2824, by M. A. Levy, et al, M. A. Levy, et al. describes the mechanism of enzyme inhibitor interation in the inhibition or rat liver steroid 5α reductase by 3-androstene-3-carboxylic acids;

3. *J. Med. Chem.* (1990) Vol. 33, pp. 943–950 (1990), by D. A. Holt, et al, describes the inhibition of steroid 5α reductase by unsaturated 3-carboxysteroids;

4. *J. Steroid Biochem,* Vol. 34, Nos. 1–6, pp. 571–575 (1989), by M. A. Levy, et al, describes the interaction mechanism between rat prostatic steroid 5-alpha reductase and 3-carboxy-17β-substituted steroids;

5. *J. Med. Chem.* (1990) Vol. 33, pp. 937–942, by D. A. Holt, et al, describes the new steroid class of A ring aryl carboxylic acids;

6. *TIPS* (December 1989) Vol. 10, pp. 491–495, by D. W. Metcalf, et al, describes the effect of inhibitors of steroid 5α reductase in benign prostatic hyperplasia, male pattern baldness and acne; and 7. EPO Publn. No. 0 289 327, to D. A. Holt, et al. (SmithKline Beckmann) describes steroidal 3-carboxylic acid derivatives as useful 5α reductase inhibitors.

8. EPO Publn. No. 0 343 954 A3, to D. A. Holt, et al., (SmithKline Beckmann) describes steroidal 3-carboxylic acid derivatives as useful 5-α-reductase inhibitors.

9. EPO Publn. No. 0 465 142 A1, to G. H. Rasmusson, et al, (Merck & Co. Inc.) describes steroidal 3-carboxylic acid derivatives as useful 5α-reductase inhibitors.

However, none of the above references specifically suggest that any of the novel steroidal 17α or 17β-substituted acyl-3-carboxy-androsta-3,5-diene compounds of the present invention would have utility as potent testosterone 5-α-reductase inhibitors.

SUMMARY OF THE INVENTION

This invention relates to a compound of the formula I:

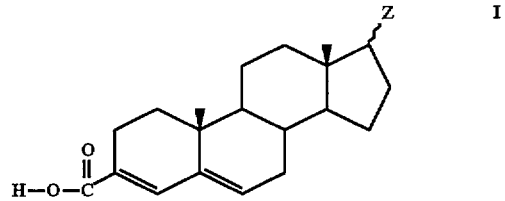

wherein
Z is α or β

in which
R is substituted cycloalkyl or substituted aryl where
  a) substituted cycloalkyl is nonaromatic, unsaturated or saturated, cyclic or polycyclic $C_3$–$C_{12}$, optionally containing one or more heteroatoms, and substituted with one or more halogens; and
  b) substituted aryl is cyclic or polycyclic aromatic $C_3$–$C_{12}$, optionally containing one or more heteroatoms, provided that when C is 3 the aromatic ring contains at least two heteroatoms, and when C is 4 the aromatic ring contains at least one heteroatom, and substituted with one or more halogens; and pharmaceutically acceptable salts, hydrates, solvates and esters thereof.

The invention also is a method for inhibiting 5-α-reductase activity in mammals, including humans, that comprises administering to a subject an effective amount of a presently invented 5-α-reductase inhibiting compound. In a further aspect of the invention there are provided novel intermediates and novel processes useful in preparing the presently invented 5-α-reductase inhibiting compounds. Included in the present invention are pharmaceutical compositions comprising a pharmaceutical carrier and compounds useful in the methods of the invention. Also included in the present invention are methods of co-administering the presently invented 5-α-reductase inhibiting compounds with further active ingredients.

DETAILED DESCRIPTION OF THE INVENTION

The compounds of this invention that inhibit 5-α-reductase have the following Formula (I):

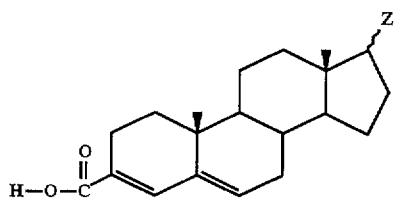

wherein

Z is α or β

in which

R is substituted cycloalkyl or substituted aryl where
  a) substituted cycloalkyl is nonaromatic, unsaturated or saturated, cyclic or polycyclic $C_3$–$C_{12}$, optionally containing one or more heteroatoms, and substituted with one or more halogens; and
  b) substituted aryl is cyclic or polycyclic aromatic $C_3$–$C_{12}$, optionally containing one or more heteroatoms, provided that when C is 3 the aromatic ring contains at least two heteroatoms, and when C is 4 the aromatic ring contains at least one heteroatom, and substituted with one or more halogens; and pharmaceutically acceptable salts, hydrates, solvates and esters thereof.

Preferred among the presently invented compounds are those having the following Formula (II):

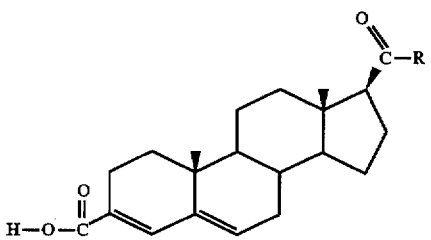

R is substituted cycloalkyl or substituted aryl where
  a) substituted cycloalkyl is nonaromatic, unsaturated or saturated, cyclic or polycyclic $C_3$–$C_{12}$, optionally containing one or more heteroatoms, and substituted with one or more halogens; and
  b) substituted aryl is cyclic or polycyclic aromatic $C_3$–$C_{12}$, optionally containing one or more heteroatoms, provided that when C is 3 the aromatic ring contains at least two heteroatoms, and when C is 4 the aromatic ring contains at least one heteroatom, and substituted with one or more halogens and pharmaceutically acceptable salts, hydrates, solvates and esters thereof.

Preferred among the presently invented Formula II compounds are those in which

R is
  a) $C_3$–$C_8$ nonaromatic, unsaturated or saturated, cycloalkyl, substituted with one or more halogens; or
  b) $C_6$–$C_{12}$ aryl, substituted with one or more halogens; and pharmaceutically acceptable salts, hydrates, solvates and esters thereof.

Particularly preferred among Formula II compounds are those in which

R is
  a) $C_6$-aryl substituted with one or more halogens; and pharmaceutically acceptable salts, hydrates, solvates and esters thereof.

Particularly preferred among Formula II compounds are those in which the halogens are fluorines.

Particularly preferred among formula II compounds is:
  17β-(4-fluorobenzoyl)-androsta-3,5-diene-3-carboxylic acid, and pharmaceutically acceptable salts, hydrates, solvates and esters thereof.

The term "α", as used herein, follows standard chemical terminology and means down or that the corresponding substituent is attached below the plane of the paper.

The term "β", as used herein, follows standard chemical terminology and means up or that the corresponding substituent is attached above the plane of the paper.

As used herein $C_x$–$C_y$ is meant a moiety having from x to y carbons.

Examples of aryl substituted aryl as used herein include: fluorophenyl, trifluoromethylphenyl and difluorophenyl.

Preferred examples of aryl and substituted aryl as used herein include: 4-fluorophenyl, 4-trifluoromethylphenyl, and 3,5-difluorophenyl.

By the term "$C_6$–$C_{12}$ aryl" as used herein, unless otherwise defined, is meant phenyl, naphthyl, 3,4-methylenedioxyphenyl, pyridyl, or biphenyl.

By the term "$C_6$aryl" as used herein, unless otherwise defined, is meant phenyl.

By the term "substituted" as used herein, unless otherwise defined, is meant that the subject chemical moiety has one or more halogen substituents.

Examples of cycloalkyl and substituted cycloalkyl as used herein include: 4-fluoro-cyclohexyl and 2-fluorocyclohexyl.

By the term "heteroatom" as used herein is meant oxygen, nitrogen or sulfur.

By the term "halogen" as used herein is meant a substituent selected from bromide, iodide, chloride and fluoride.

By the term "treating" and derivatives thereof as used herein, is meant prophylatic or therapeutic therapy.

By the term "metal-catalyzed coupling reaction" as used herein is meant that the prepared 3-trifluoromethyl sulfonylate or 3-fluorosulfonylate compound is reacted in a suitable organic solvent, preferably toluene, dimethylsulfoxide, dichloroethane, dimethylformamide or THF; with a base, preferably a tertiaryamine base such as triethylamine, pyridine or tributylamine; a $C_1$–$C_6$alcohol (when an ester is desired) or a $C_1$–$C_6$carboxylic acid salt, preferably KOAc (when an acid is desired) and a phosphine, such as bis (diphenylphosphino)alkane, preferably 1,3 bis (diphenylphosphino)propane, tri-o-tolyphosphine or 1,1-bis (diphenylphosphino)ferrocene (dppf) and a metal catalyst, preferably a palladium catalyst such as palladium (II) acetate or palladium (II) chloride or bis(triphenylphosphine) palladium II acetate, thereby forming a metalated complex, and subsequently adding a coupling reagent.

By the term "coupling reagent" as used herein is meant a compound which is capable of reacting with said metalated complex to form an ester or a carboxylic acid substituent. Carbon monoxide is a preferred coupling reagent which when added to the metal-catalyzed coupling reaction, as described herein, yields the desired carboxylic acid group.

Compounds of Formula (I) and compounds of Formula (V) are included in the pharmaceutical compositions of the invention and used in the methods of the invention. Where a —COOH group is present, pharmaceutically acceptable esters can be employed, for example methyl, ethyl, pivaloyloxymethyl, and the like and those esters known in the art for modifying solubility or hydrolysis characteristics for use as sustained release or prodrug formulations.

The term "α-receptor antagonist", as used herein, refers to a known class of alpha-andrenergic receptor antagonist comounds, such as described in Lafferty, et al. U.S. Pat. No. 4,963,547, which are utilized in treating vascular disorders such as diabetes, cardiovascular disease, benign prostatic hypertrophy and ocular hypertension.

Preferred alpha-andrenergic receptor antagonists for use in the compositions and methods of the invention include amsulosin, terazosin, doxazosin, alfuzosin, indoramin, prazosin, 7-chloro-2-ethyl-3,4,5,6-tetrahydro-4-methylthieno[4,3,2-ef][3]-benzazepine and 8-{3-[4-(2-methoxyphenyl)-1-piperazinyl]-propylcarbamoyl}-3-methyl-4-oxo-2-phenyl-4H-1-benzopyran.

By the term "amsulosin" as used herein is meant a compound of the structure

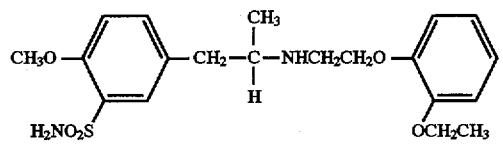

and salts, hydrates and solvates thereof.

Chemically, amsulosin is designated as (−)-(R)-5-[2-[[2-(O-ethoxyphenoxy)ethyl]amino]propyl]-2-methoxybenzenesulfonamide.

Amsulosin is disclosed in U.S. Pat. No. 4,703,063 and claimed in U.S. Pat. No. 4,987,125 as being useful in treating lower urinary tract dysfunction.

By the term "terazosin" as used herein is meant a compound of the structure

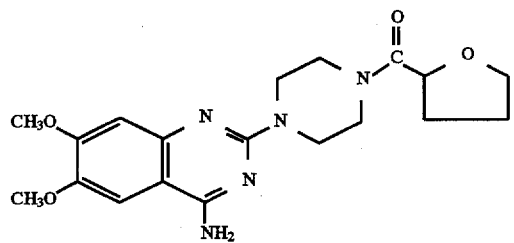

and salts, hydrates and solvates thereof.

Chemically, terazosin is designated as 1-(4-amino-6,7-dimethoxy-2-quinazolinyl)-4-[(tetrahydro-2-furoyl)carbonyl]piperazine. Terazosin is disclosed in U.S. Pat. No. 4,251,532.

By the term doxazosin as used herein is meant a compound of the formula

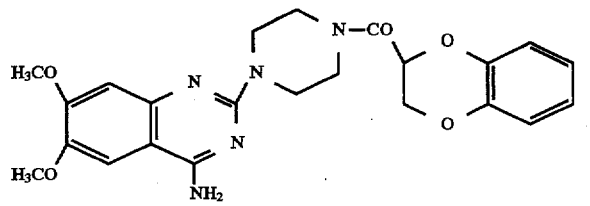

and salts, hydrates and solvates thereof.

Chemically "doxazosin" is designated as 1-(4-amino-6,7-dimethoxy-2-quinazolinyl)-4-[(2,3-dihydro-1,4-benzodioxin-2-yl)carbonyl]-piperazine.

Doxazosin is disclosed in U.S. Pat. No. 4,188,390.

By the term "alfuzosin" as used herein is meant a compound of the formula

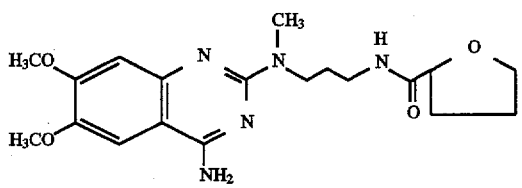

and salts, hydrates and solvates thereof.

Chemically alfuzosin is designated as N-[3-[(4-amino-6,7-dimethoxy-2-quinazolinyl)methylamino]propyl] tetrahydro-2-furancarboxamide.

Alfuzosin is disclosed in U.S. Pat. No. 4,315,007.

By the term "indoramin" as used herein is meant a compound of the formula

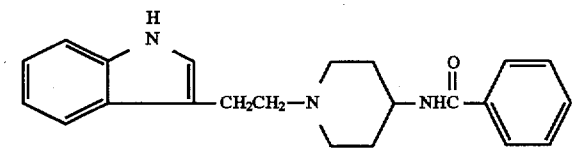

and salts, hydrates and solvates thereof.

Chemically indoramin as designated N-[[1-[2-(1H-indol-3-yl)ethyl]-4-piperidinyl]benzamide.

Indoramin is disclosed in U.S. Pat. No. 3,527,761.

By the term "prazosin" as used herein is meant a compound of the formula

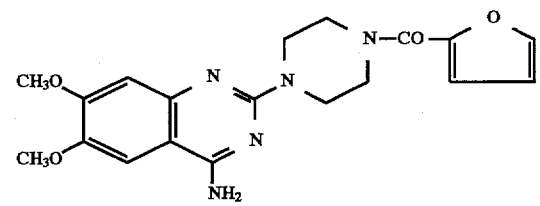

and salts, hydrates and solvates thereof.

Chemically prazosin is designated as 1-(4-amino-6,7-dimethoxy-2-quinazolinyl)-4-(2-furanylcarbonyl)piperazine.

Prazosin is disclosed in U.S. Pat. No. 3,511,836.

"7-chloro-2-ethyl-3,4,5,6-tetrahydro-4-methylthieno[4,3,2-ef][3]benzazepine" as used herein is meant a compound of the structure

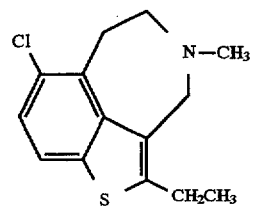

and salts, hydrates and solvates thereof.

7-chloro-2-ethyl-3,4,5,6-tetrahydro-4-methylthieno[4,3,2-ef][3]benzazepine is disclosed in U.S. Pat. No. 5,006,521. Additionally, all compounds disclosed in U.S. Pat. No. 5,006,521 as alpha-adrenergic receptor antagonist are preferred alpha-adrenergic receptor antagonist as used herein.

"8-{3-[4-(2-methoxyphenyl)-1-piperazinyl)-propylcarbamoyl}-3-methyl-4-oxo-2-phenyl-4H-1- benzopyran" as used herein is meant a compound of the structure

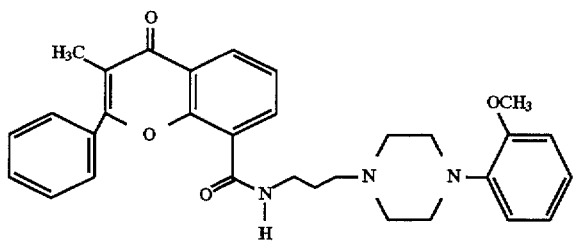

and salts, hydrates end solvates thereof.

8-{3-4-(2-methoxyphenyl)-1-piperazinyl]-propylcarbamoyl}-3-methyl-4-oxo-2-phenyl-4H-1-benzopyran is disclosed in EPO Publn. No. 05889.45 A1, to Leonardi, et al., (Recordati S. A.).

Additionally all compounds disclosed in EPO Publn. No. A1, as alpha-adrenergic receptor antagonists are preferred alpha-adrenergic receptor antagonists as used herein.

Persons skilled in the art can readily determine if a compound other than one specifically referred to herein is a alpha-andrenergic receptor antagonist by utilizing the assay described in Lafferty I. Thus, all such compounds are included within the scope of the term "alpha-andrenergic receptor antagonist" as used herein.

By the term "minoxidil" as used herein is meant the compound of the formula:

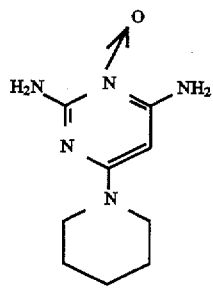

chemically minoxidil is designated as 2,4-pyrimidineadiamine, 6-(1-piperidinyl)-,3-oxide. Minoxidil is the active ingredient in Rogaine® which is sold as topical solution for stimulating hair growth by the Upjohn Company, Kalamazoo, Mich.

The term "aromatase inhibitor", as used herein, refers to a known class of compounds, steroidal and non-steroidal, which prevent the conversion of androgens to estrogens, such as described in Gormley et al. International Publication Number WO 92/18132. Aromatase inhibitors are disclosed in Gormley et al. as having utility in treating benign prostatic hyperplasia when used in combination with a 5-α-reductase inhibitor.

A preferred aromatase inhibitor for use in the compositions and methods of the invention 4-(5,6,7,8-tetrahydroimidazo-[1,5-α]pyridin-5-yl)benzonitrile (fadrazole). Fadrazole is disclosed in U.S. Pat. No. 4,728, 645. Additionally, all compounds disclosed in Gormley, et al. International Publication No. WO 92/18132 as having aromatase inhibiting activity are preferred aromatase inhibitors as used herein.

As used herein, when a 5-α-reductase inhibitor, as described herein and a further active ingredient or ingredients are utilized together, said 5-α-reductase inhibitor can be co-administered with said further active ingredient or ingredients.

By the term "co-administering" and derivatives thereof as used herein is meant either simultaneous administration or any manner of separate sequential administration of a 5-α-reductase inhibiting compound, as described herein, and a further active ingredient or ingredients, such as other compounds known to treat the disease states of acne vulgaris, seborrhea, female hirsutism, male pattern baldness, benign prostate hypertrophy or prostatic adenocarcinoma or compounds known to have utility when used in combination with 5-α-reductase inhibitors. Preferably, if the administration is not simultaneous, the compounds are administered in a close time proximity to each other. Furthermore, it does not matter if the compounds are administered in the same dosage form, e.g. one compound may be administered topically and another compound may be administered orally.

The novel compounds of Formula (II) of the present invention can be prepared by methods outlined in schemes 1–3 below and in the examples from the known and readily available steroid acid of the formula:

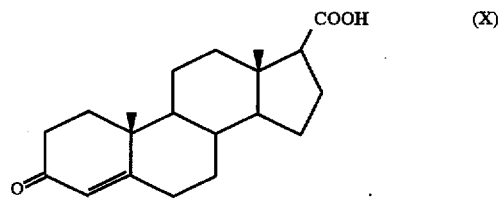

Scheme I

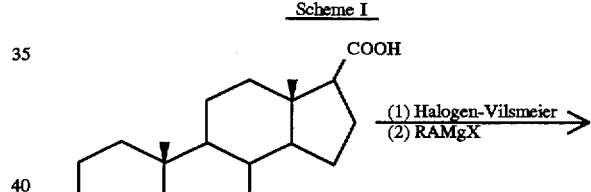

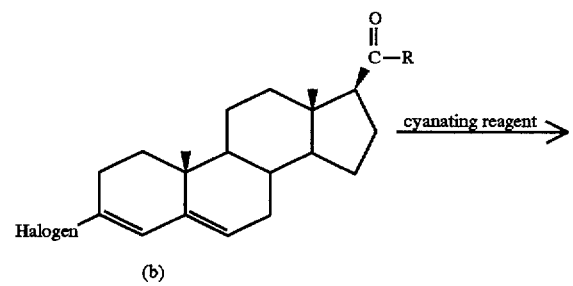

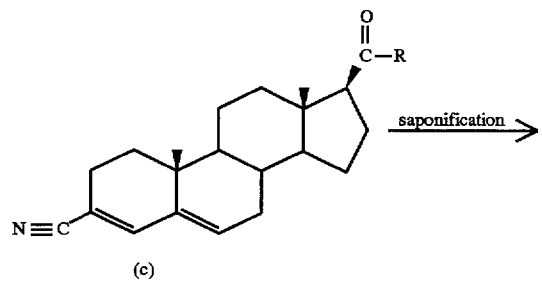

Scheme I

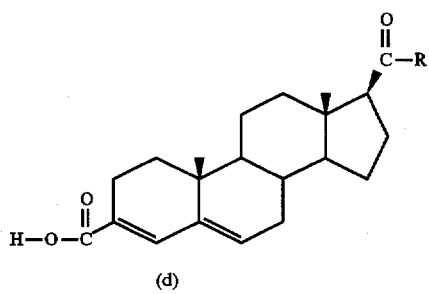

Scheme I outlines formation of Formula II compounds. As used in scheme I compound (b) is prepared from compound (a) by treating (a) with halogen-Vilsmeier reagent, described hereinbelow, in an appropriate solvent, preferably methylene chloride followed by quenching with excess Grignard reagent, described hereinbelow. The 3-cyano derivative (c) is produced by treating (b) with a cyanating reagent, described hereinbelow, in an appropriate solvent, preferably dimethylformamide. The 17-acyl derivative (c) is saponified, described hereinbelow, to yield compounds (d).

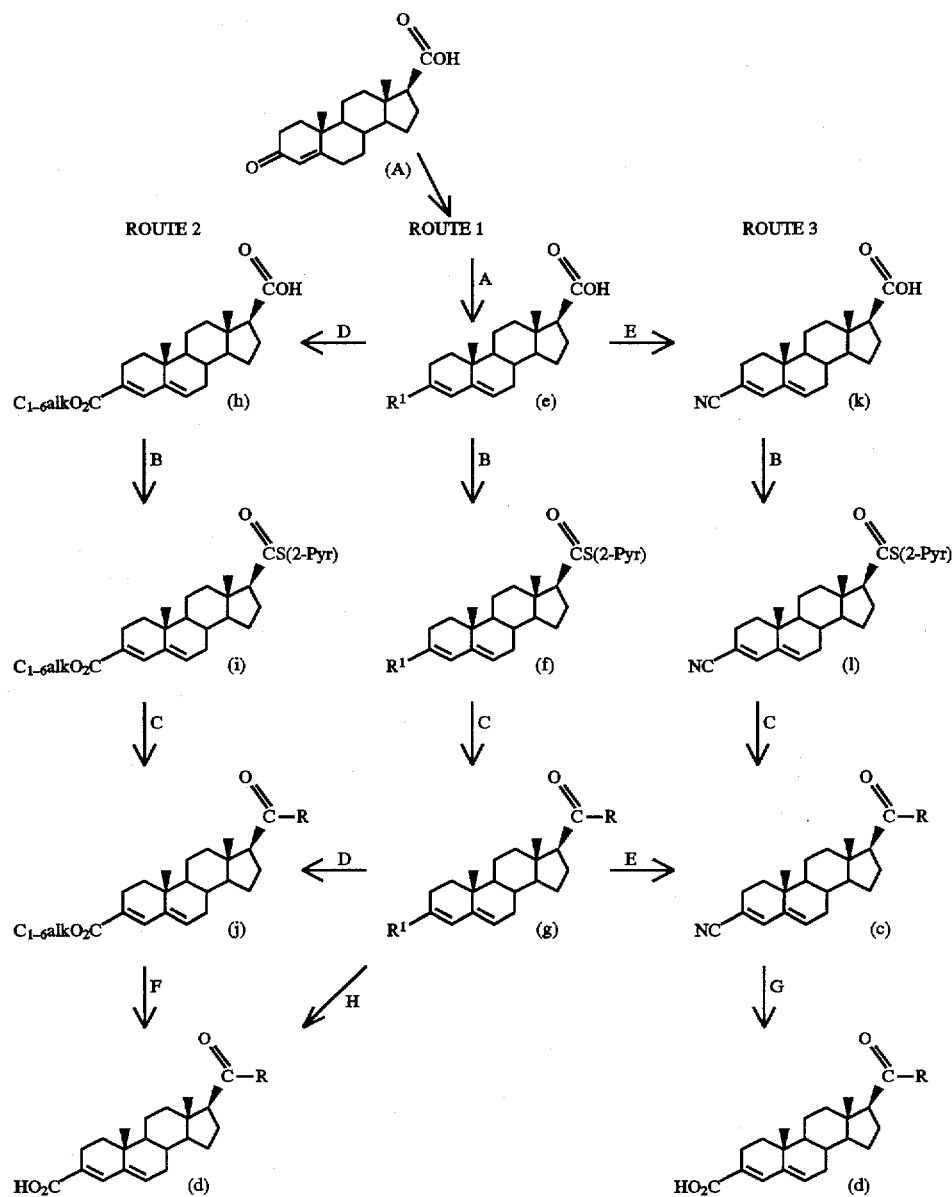

Scheme II outlines formation of Formula II compounds. As used in Scheme II is as described in Formula IV, $R^1$ is $CF_3O_2SO-$ or $FO_2SO-$. As used in scheme II in the alkylation process (step C), the pyridylthio ester is reacted with an Li-R or an XMgR (X=Cl, Br) Grignard reagent (as described hereinbelow), preferably 4-fluorophenylmagnesium bromide to form the desired product, preferably 17β-(4-fluorobenzoyl)-androsta-3,5-diene-3-carboxylic acid, in one or two steps.

In Route 1, the enone acid (a) is converted to the 3-trifluoromethylsulfonylate or 3-fluorosulfonylate derivative (e) (step A) by treating (a) with trifluoromethylsulfonylate anhydride or fluorosulfonic anhydride and an amine base, such as pyridine, preferably 2,5 di-t-butyl-3-methyl-pyridine, in an appropriate organic solvent, preferably dichloromethane at about -20° C. to 20° C., preferably 0°.

The activated ester (f) is produced (step B) by treating (e) with 2,2-dithiopyridyl and triphenylphosphine in an appropriate organic solvent solution preferably, tetrahydrofuran/toluene at room temperature for about 8-14 hours.

The 17-acyl derivative (g) is produced (step C) by treating (f) with a Grignard reagent, described hereinbelow, in tetrahydrofuran or diethyl ether solvent, at a temperature of about -50° to -70°, for 1-16 hours.

The 3-alkyl ester (j) is produced (step D) by treating (g) under carbonylation conditions, preferably by bubbling carbon monoxide gas through a solution of (g) in an appropriate organic solvent, preferably methanol, containing palladium acetate catalyst, triphenylphosphine, and a tertiary organic amine preferably triethylamine at about room temperature for 1-16 hours. Compound (j) next is reacted with a suitable base, preferably potassium carbonate and acidified (step F) to yield compounds (d).

Compounds (d) can also be produced (step H) by treating (g) under carboxylation conditions, preferably by bubbling carbon monoxide gas through a solution of (g) in appropriate non-alcoholic solvent, preferably DMF, containing a palladium catalyst, preferably bis(triphenylphoshine)palladium II diacetate, and a base, preferably potassium acetate, preferably at increased temperatures.

Route 2 involves converting the starting steroidal acid (a) to the 3-trifluoromethylsulfonylate or the 3-fluorosulfonylate derivative (e) by the above-described step A; carbonylating (e) to (h) by step D; forming the activated 2-pyridylthio ester (i) by step B; forming the 17-acyl compound (j) by step C; and hydrolyzing the 3-ester to the 3 acid final product (d) by step F.

Route 3 involves converting the starting steroid acid (a) to the 3-trifluoromethylsulfonylate or the 3-fluorosulfonylate derivative (e) by the above-described step A. The 3-cyano derivative (k) is produced (step E) by treating (e) with a cyanating agent (as described hereinbelow) in an appropriate solvent, preferably dimethylformamide. The activated 2-pyridylthio derivative (l) is prepared from (k) by step B. Forming the 17-acyl compound (c) involves reacting (l) by step C. The 17-acyl derivative (c) is saponified (step G) (as described herein) to yield compounds (d).

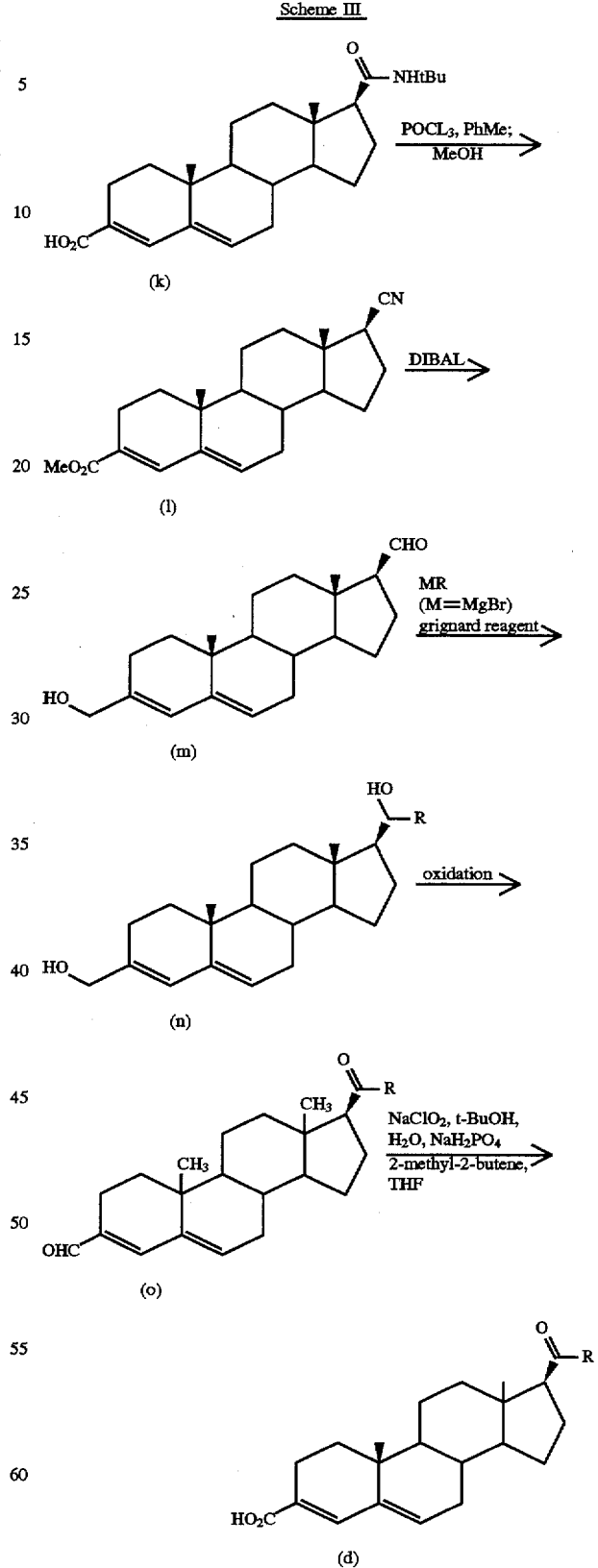

Scheme III outlines formation of Formula II compounds. As used in Scheme III, compound (l) is prepared from compound (k) by treatment with phosphorusoxychloride in toluene followed by treatment with methanol.

Formula (l) compounds are reacted with a reducing agent, preferably diisobutylaluminum hydride, to yield formula (m) compounds.

Formula (n) compounds are produced by treating formula (m) compounds with a Grignard Reagent (as described in Scheme II) in tetrahydrofuran or diethylether solvent, at a temperature of about −50° C. to −70° C., for 1–16 hours.

Formula (o) compounds are prepared by oxidation of formula (n) compounds. Preferably said oxidation will utilize tetrapropylammoninm peruthenate or a Jone's reagent.

Formula (d) compounds are prepared by oxidation of formula (o) compounds. Preferably said oxidation will utilize sodium chlorite.

As used herein Grignard reagents of the type, XMgR, for all of the species included within the scope of this invention, are available or can be made readily by one skilled in the art.

For example, where a R is fluorophenyl, this can be derived by starting with an appropriate bromo-fluorophenyl, e.g. 4-bromo-phenylfluoride.

Other halo substituted benzenes to form the appropriate Grignard reagent useful in the instant invention will be obvious to one skilled in the art from this disclosures.

Formula I compounds in which Z is in the α position are prepared from compounds which contain the corresponding β substituent by the General Method below.

General Method A

To a stirred solution of a substituted 17β steroidal 5α-reductase inhibiting compound of Formula (II) in an appropriate solvent, preferably ethylene glycol or dimethyl sulfoxide, is added a base such as a hydroxide or alkoxide base, preferably sodium hydroxide, potassium hydroxide or sodium methoxide, at a temperature over 100° C. preferably at reflux temperatures to yield the corresponding α epimer, after isolation and work up.

In determining the appropriate solvent for conducting the epimerization, dimethyl sulfoxide or other non-reactive high boiling solvents are preferred when the stating 17β 5α-reductase inhibiting steroidal compound contains reactive substituents or reactive unsaturated bonds that are, for example, subject to nucleophilic attack and ethylene glycol, or other reactive high boiling solvents can be used when the reactivity of the substituents or any unsaturated bonds of the starting 17β 5α-reductase inhibiting steroidal compound is not a consideration.

Also within the scope of the present invention are the ketone reduction products of Formula (I) compounds, the secondary alcohols of the formula:

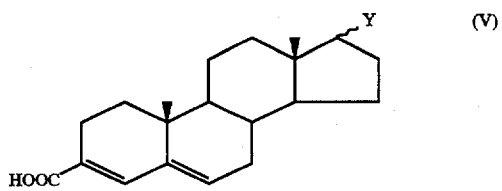

(V)

wherein

Y is α or β

in which

R is substituted cycloalkyl or substituted aryl, where
  a) substituted cycloalkyl is nonaromatic, unsaturated or saturated, cyclic or polycyclic $C_3$–$C_{12}$, optionally containing one or more heteroatoms, and substituted with one or more halogens; and
  b) substituted aryl is cyclic or polycyclic aromatic $C_3$–$C_{12}$, optionally containing one or more heteroatoms, provided that when C is 3 the aromatic ring contains at least two heteroatoms, and when C is 4 the aromatic ring contains at least one heteroatom, and substituted with one or more halogens; and pharmaceutically acceptable salts, hydrates solvates and esters thereof.

Particularly preferred among the presently invented ketone reduction poducts described above are the secondary alcohols wherein the 17

substituent is attached in the β position.

These compounds can be made by conventional sodium borohydride reduction of the carbonyl, without epimerization or reducing the carboxyl in Ring A or the 3,5-double bonds.

The borohydride reduction can be carried out in e.g. water or aqueous methanol, at a temperature of room temperature to 50° C. and the product then isolated and purified by conventional means. The compounds are also active as 5-alpha reductase inhibitors.

By the term "halogen-Vilsmeier reagent" as used herein is meant a halogenated disubstituted formamide reagent of the structure:

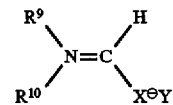

wherein $R^9$ and $R^{10}$ are independently selected from an alkyl, aryl or arylalkyl group; and X is Br or I; and y is a counter ion, which is prepared by
  a) reacting, preferably at reduced temperatures, a chloride source such as oxalyl chloride or thionyl chloride, with a disubstituted formamide reagent, such as a dialkyl substituted formamide reagent preferably dimethylformamide, in an appropriate solvent, preferably methylene chloride, to form a chloro-Vilsmeier reagent, said chloro-Vilsmeier reagent being reacted in situ, preferably at reduced temperatures, with a bromide source or an iodine source, preferably hydrogen bromide gas or
  b) reacting, preferably at reduced temperatures, a bromide source or an iodide source, preferably oxalyl bromide, with a disubstituted formamide reagent, such as a dialkyl substituted formamide reagent preferably dimethylformamide in an appropriate solvent, preferably methylene chloride.

By the term "reduced temperature" as used herein is meant below 25° C., preferably between −15° and 15° C., most preferably between 0° and 10° C.

By the term "cyanating reagent" as used herein and in the claims is meant a compound or reagents which are capable of reacting with a halogenated moiety to form a cyanated moiety under appropriate conditions.

Preferably said cyanated moiety is prepared by reacting the corresponding halogenated moiety with a cyanating agent in an appropriate solvent, such as N,N-dimethyl-N,N-propylene urea (DMPU), N,N-dimethylformamide (DMF) or N-methyl-2-pyrrolidinone (NMP), preferably DMF, at increased temperatures.

By the term "saponifying" and derivatives thereof as used herein and in the claims is meant a compound or reagent or a series of reagents which are capable of reacting with a nitrile to form a carboxylic acid substituted moiety under appropriate conditions. Preferably said carboxylic acid substituted moiety is prepared by reacting the corresponding cyanated moiety with a hydroxide base, preferably aqueous sodium hydroxide, in an appropriate solvent, such as; ethylene glycol, isopropyl alcohol or ethanol, preferably ethanol, at increased temperatures with subsequent acidification.

By the term "increased temperatures" as used herein and in the claims is meant above 25° C., preferably at reflux temperatures.

Preferably cyanating reagents for use in the presently disclosed processes utilize cyanide complexes such as described in Richard C. Larock, *Comphrehensive Organic Transformations: A Guide to Functional Group Preparations*. Pub: VCH Publishers, Inc. (1989) P. 861. An example of a cyanide complex as used herein is the in situ co-mixture of KCN, NiBr$_2$(PPh$_3$)$_2$, Zn, PPh$_3$. Other examples include: Co(CN)$_3^{3-}$; K$_4$Ni$_2$(CH)$_6$, KCN; KCN, cat Pd(PPh$_3$)$_4$; Co(CN)$_5^{3-}$; CuCN and NaCu(CN)$_2$. As used herein the term "NaCu(CN)$_2$" refers to the reagent formed by co-mixing CuCN and NaCN in situ.

Preferred among the above cyanating complexes are CuCN and NaCu(CN)$_2$.

Particularly preferred among the above cyanating complexes is NaCu(CN)$_2$.

Preferably said NaCu(CN)$_2$ complex is prepared by adding 1 molar equivalent of sodium cyanide to cuprous cyanide in situ.

By the term "solvent" or "appropriate solvent" as used herein and the in the claims is meant a solvent such as methylene chloride, ethylene chloride, chloroform, ethylene glycol, carbon tetrachloride, tetrahydrofuran (THF), ethyl ether, toluene, ethyl acetate, hexane, dimethylsulfoxide (DMSO), N,N'-dimethyl-N,N'-propylene urea, N-methyl-2-pyrrolidinone, methanol, isopropylalcohol, dimethylformamide (DMF), water, pyridine, quinoline or ethanol.

Pharmaceutically acceptable salts, hydrates and solvates of Formula (I) and Formula (V) compounds are formed, where appropriate, by methods well known to those of skill in the art.

In preparing the presently invented compounds of Formula (I), novel intermediates of the following Formula (IV) are synthesized;

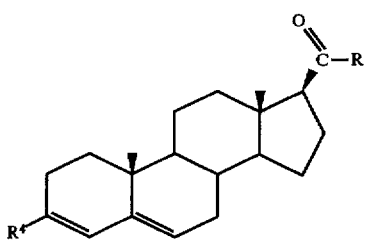
(IV)

in which
R is as defined in Formula (II), and

R$^4$ is fluorosulfonyloxy, halogen, cyano, or —CHO.

Also prepared in synthesing the presently invented Formula I compounds were novel intermediates of the Formula

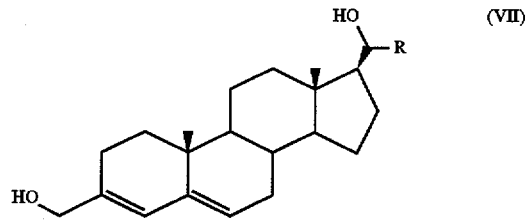
(VII)

in which
R is as defined in Formula I.

A preferred process for preparing a compound of Formula (II)

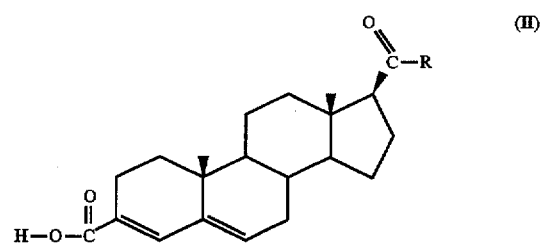
(II)

in which
R is as defined in Formula (II) above and pharmaceutically acceptable salts, hydrates, solvates and esters thereof comprises reacting a compound of the formula

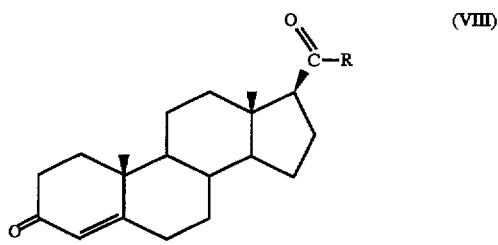
(VIII)

in which
R is as defined in Formula (II) with fluorosulfonic anhydride and a base, preferably, 2,5-t-butyl-3-methylpyridine, in a solvent, preferably dichloromethane, to form a compound of the formula

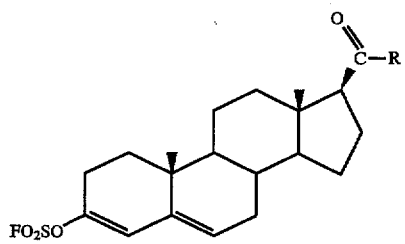

in which
R is as described above and subsequently reacting said compound in a metal-catalyzed coupling reaction in the presence of an appropriate coupling reagent, preferably, carbon monoxide followed by an optional, if applicable, hydrolysis reaction to form a compound of Formula II, and thereafter optionally forming a pharmaceutically acceptable salt, hydrate or solvate thereof.

The above formula (VIII) compounds are prepared by first activating the 17-position carboxyic acid substituent of compounds of structure (X), as described herein, preferably with an acid chloride, such as thionylchloride or by forming a thiopyridylester by reaction with 2,2-dithiopyridyl, and then treating with a Grignard reagent as described herein.

A preferred process for preparing a compound of Formula II

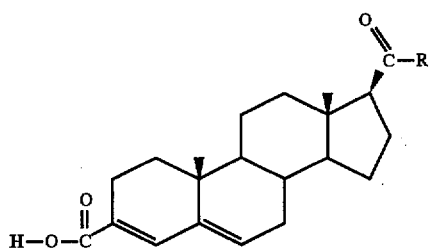

in which
R is a defined in Formula (II) and pharmaceutically acceptable salts, hydrates, solvates and esters thereof comprises reacting a compound of the formula

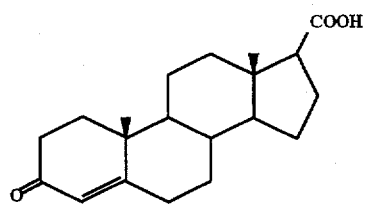

in the presence of a halogen-Vilsmeier reagent and a solvent then quenching with excess Grignard reagent to form a compound of the formula

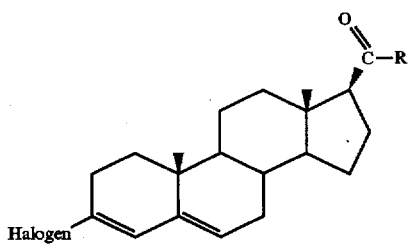

in which
R is as described above and subsequently, in an appropriate solvent, reacting said compound with a cyanating reagent to form a compound of the formula

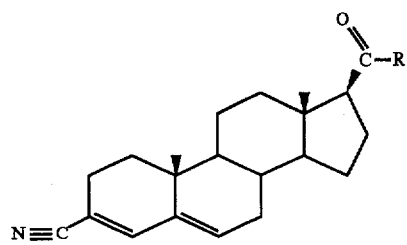

in which
R is as defined above and subsequently saponifying said compound to form a compound of Formula II and thereafter optionally forming a pharmaceutically acceptable salt, hydrate or solvate.

A preferred process for the preparation of a compound of the Formula

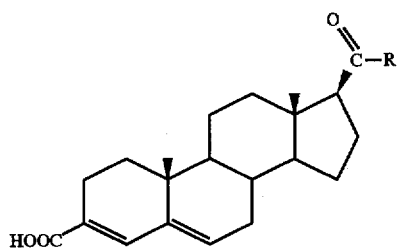

in which
R is as defined in Formula (II); and
pharmaceutically acceptable salts, hydrates, solvates and esters thereof which comprises either
(i) oxidation of a compound of the Formula (VII)

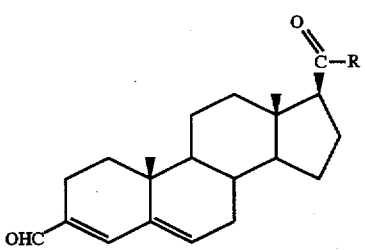

(VII)

in which
R is as defined in Formula (IV) or
(ii) reacting a compound of the Formula (XI)

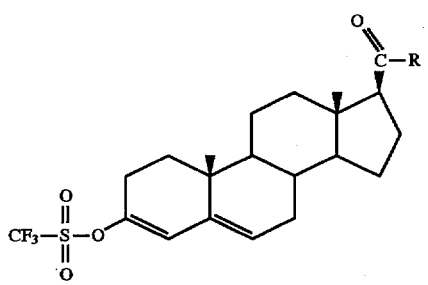

(XI)

in which
R is as described above, in a metal-catalyzed coupling reaction in the presence of an appropriate coupling reagent, preferably, carbon monoxide followed by an optional, if applicable, hydrolysis reaction or
(iii) hydrolyzing a compound of the Formula (XII)

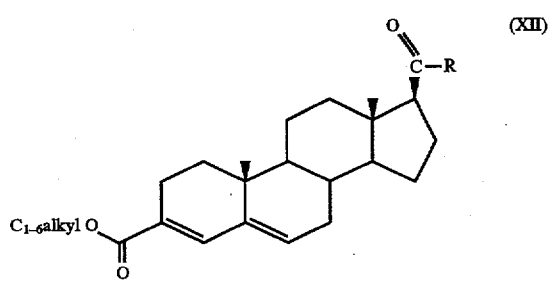

(XII)

in which
R is as described above,
and thereafter optionally forming a pharmaceutically acceptable salt, hydrate or solvate thereof.

Because the presently invented pharmaceutically active compounds inhibit steroid 5-α-reductase activity, they have therapeutic utility in treating diseases and conditions wherein decreases in DHT activity produces the desired therapeutic effect. Such diseases and conditions include acne vulgaris, seborrhea, female hirsutism, male pattern baldness, prostate diseases such as benign pro static hypertrophy, and prostatic adenocarcinoma.

In determining potency in inhibiting the human 5α-reductase enzyme, the following procedure was employed:

Preparation of membrane particulates used as source for recombinant steroid 5α-reductase isozyme 1.

Chinese hamster ovary (CHO) cells containing expressed, recombinant human steroid 5α-reductase isoenzyme 1 (Andersson, S., Berman, D. M., Jenkins, E. P., and Russell, D. W. (1991) Nature 354 159–161) were homogenized in 20 mM potassium phosphate, pH 6.5, buffer containing 0.33M sucrose, 1 mM dithiothreitol, and 50 µM NADPH (buffer A) using a Dounce glass-to-glass hand homogenizer (Kontes Glass Co., Vineland, N.J.). Membrane particulates were isolated by centrifugation (100,000×g at 4° C. for 60 minutes) and resuspended in 20 mM potassium phosphate, pH 6.5, containing 20% glycerol, 1 mM dithiothreitol, and 50 µM NADPH (buffer B). The suspended particulate solution was stored at –80° C.

Preparation of prostatic membrane particulates used as source for steroid 5α-reductase isozyme 2.

Frozen human prostates were thawed and minced into small pieces (Brinkmann Polytron (Sybron Corp., Westbury, N.Y.). The solution was sonicated for 3 to 5 minutes with a Sonifier (Branson Sonic Power Co.) followed by hand homogenization in a Dounce hand homogenizer. Prostatic particles were obtained by differential centrifugation at 600 or 1000×g for 20 minutes and 140,000×g for 60 minutes at 4° C. The pellet obtained from the 140,000×g centrifugation was washed with 5 to 10 tissue volumes of the buffer described above and centrifuged at 140,000×g. The resulting pellet was suspended in buffer B and the particulate suspension was stored at –80° C.

Preparation of membrane particulates used as source for recombinant steroid 5-α-reductase isozyme 2.

Chinese hamster ovary (CHO) cells containing expressed, recombinant human steroid 5-α-reductase isozyme 2 were homogenized in 20 mM potassium phosphate, pH 6.5, buffer containing 0.33M sucrose, 1 mM dithiothreitol, and 50 µM NADPH (buffer A) using a Douce hand homogenizer. Membrane particulates containing the recombinant human enzyme were isolated by centrifugation (100,000×g at 4° C. for 60 minutes) and resuspended in 20 mM potassium phosphate, pH 6.5 containing 20% glycerol, 1 mM dithiothreitol, and 50 µM NADPH (buffer B). The suspended particulate solution was stored at –80° C. until used.

Assay for enzymes activities and inhibitors potency.

A constant amount of [$^{14}$C]testosterone (50 to 55 mCi/mmol) in ethanol and varying amounts of potential inhibitor in ethanol were deposited in test tubes and concentrated to dryness in vacuo. To each tube was added buffer, 10 µL (recombinant isoenzyme 1 or isoenzyme 2) or 20 µL, (isoenzyme 2 from human prostate tissue) of 10 mM NADPH and an aliquot of asteroid 5α-reductase preparation to a final volume of 0.5 mL. Assays for human steroid 5α-reductase isoenzyme 1 were conducted with a sample of the recombinant protein expressed in CHO cells in 50 mM phosphate buffer, pH 7.5 while assays of isoenzyme 2 were conducted with a suspension of human prostatic particulates and/or recombinant protein expressed in CHO cells in 50 mM citrate buffer at pH 5.0.

After incubating the solution at 37° C. for 20 or 30 minutes the reaction was quenched by the addition of 4 mL ethyl acetate and 0.25 µmol each of testosterone, 5α-dihydrotestosterone, androstanediol, and androstanedione as carriers. The organic layer was removed to a second test tube and evaporated to dryness in a Speed Vac. The residue was dissolved in 40 µL chloroform, spotted on an individual lane of a 20×20 cm prechannelled silica gel TLC plate (Si 250F-PA, Baker Chemical) and developed twice with acetone:chloroform (1:9). The radiochemical content in the bands of the substrate and the products was determined with a BIOSCAN Imaging Scanner (Bioscan Inc., Washington, D.C.). The percent of recovered radiolabel converted to product was calculated, from which enzyme activity was determined. All incubations were conducted such that no more than 20% of the substrate (testosterone) was consumed.

The experimentally obtained data was computer fit to a linear function by plotting the reciprocal of the enzyme activity (1/velocity) against the variable inhibitor concentration; apparent inhibition constants ($K_{i,app}$) were determined by the Dixon analysis (Dixon, M. (1953).

The value for the inhibition constant (Ki) was calculated from known procedures (Levy, M. (1989), *Biochemistry*, 29:2815–2824).

The pharmaceutically active compounds within the scope of this invention are useful in inhibiting steroid 5-α-reductase in a mammal, including humans, in need thereof.

A compound within the scope of this invention has been tested and has shown an activity of 85 Ki(nM) against isozyme 1 and an activity of 2 Ki(nM) against isozyme 2. Particularly preferred among the compounds of the invention and the compounds used in the invented pharmaceutical compositions and invented methods is 17β-(4-fluorobenzoyl)-androst-3,5-diene-3-carboxylic acid.

The pharmaceutically active compounds of the present invention are incorporated into convenient dosage forms such as capsules, tablets, or injectable preparations. Solid or liquid pharmaceutical carriers are employed. Solid carriers include, starch, lactose, calcium sulfate dihydrate, terra alba, sucrose, talc, gelatin, agar, pectin, acacia, magnesium stearate, and stearic acid. Liquid carriers include syrup, peanut oil, olive oil, saline, and water. Similarly, the carrier or diluent may include any prolonged release material, such as glyceryl monostearate or glyceryl distearate, alone or with a wax. The amount of solid carrier varies widely but, preferably, will be from about 25 mg to about 1 g per dosage unit. When a liquid carrier is used, the preparation will be in the form of a syrup, elixir, emulsion, soft gelatin capsule, sterile injectable liquid such as an ampoule, or an aqueous or nonaqueous liquid suspension.

The pharmaceutical preparations are made following conventional techniques of a pharmaceutical chemist involving mixing, granulating, and compressing, when necessary, for tablet forms, or mixing, filling and dissolving the ingredients, as appropriate, to give the desired oral or parenteral products.

Doses of the presently invented pharmaceutically active compounds in a pharmaceutical dosage unit as described above will be an efficacious, nontoxic quantity preferably selected from the range of 0.01–1000 mg/kg of active compound, preferably 0.1–100 mg/kg. When treating a human patient in need of steroid 5-α-reductase inhibition, the selected dose is administered preferably from 1–6 times daily, orally or parenterally. Preferred forms of parenteral administration include topically, rectally, transdermally, by injection and continuously by infusion. Oral dosage units for human administration preferably contain from 0.1 to 500 mg of active compound. Oral administration, which uses lower dosages is preferred. Parenteral administration, at high dosages, however, also can be used when safe and convenient for the patient.

The method of this invention of inhibiting steroid 5-α-reductase activity in mammals, including humans, comprises administering to a subject in need of such inhibition an effective steroid 5-α-reductase inhibiting amount of a pharmaceutically active compound of the present invention.

The invention also provides for the use of a compound of Formula (I) or a compound of Formula (V) in the manufacture of a medicament for use in the inhibition of steroid 5-α-reductase.

The invention also provides for a pharmaceutical composition for use in the treatment of benign prostate hypertrophy which comprises a compound of Formula I or a compound of Formula (V) and a pharmaceutically acceptable carrier.

The invention also provides for a pharmaceutical composition for use in the treatment of prostatic adenocarcinoma which comprises a compound of Formula I or a compound of Formula (V) and a pharmaceutically acceptable carrier.

The invention also provides for a process for preparing a pharmaceutical composition containing a pharmaceutically acceptable carrier or diluent and a compound of Formula I or a compound of Formula (V) which comprises bringing the compound of Formula I or the compound of Formula (V) into association with the pharmaceutically acceptable carrier or diluent.

No unacceptable toxicological effects are expected when compounds of the invention are administered in accordance with the present invention.

In addition, the pharmaceutically active compounds of the present invention can be co-administered with further active ingredients, such as other compounds known to treat the disease states of acne vulgaris, seborrhea, female hirsutism, male pattern baldness, benign prostate hypertrophy or prostatic adenocarcinoma or compounds known to have utility when used in combination with 5-α-reductase inhibitors. Particularly preferred is the co-administration of a 5-α-reductase inhibitor, as disclosed herein, and minoxidil for use in the treatment of male pattern baldness. Particularly preferred is the co-administration of a 5α-reductase inhibitor, as disclosed herein, and a α-receptor antagonist for use in the treatment of benign prostatic hypertrophy. Preferred is the co-administration of a 5-α-reductase inhibitor, as disclosed herein, and an aromatase inhibitor for use in the treatment of benign prostatic hypertrophy. Preferred is the co-administration of a 5-α-reductase inhibitor, as disclosed herein, a α-receptor antagonist and an aromatase inhibitor for use in the treatment of benign prostatic hypertrophy.

Without further elaboration, it is believed that one skilled in the art can, using the preceding description, utilize the present invention to its fullest extent. The following Examples are, therefore, to be construed as merely illustrative and not a limitation of the scope of the present invention in any way.

EXAMPLE 1—Corresponding to Scheme I

17β-(4-fluorobenzoyl)-androsta-3,5-diene-3-carboxylic acid (i). 17β-(4-fluorobenzoyl)-androsta-3-bromo-3,5-diene A flask under nitrogen atmosphere is charged with 100 mL of methylene chloride and 6.12 mL of dimethylformamide. The solution is cooled to 0°–5° C., and treated with 6.9 mL of oxalyl chloride while maintaining the temperature between 0°–10° C. A white precipitate formed. After stirring for one hour, 50.1 grams of hydrogen bromide gas is bubbled through the solution while maintaining the temperature between 0°–10° C. The suspension becomes a clear colorless solution. The solution is degassed by reducing the solution volume by about one-half by vacuum distillation and restoring to its original volume with methylene chloride. This concentration/refill procedure is repeated. Androst4-en-3-one-17β-carboxylic acid, 10.0 grams, is added to the resulting white suspension and the mixture is warmed to room temperature and stirred for 2 hours. The reaction mixture is quenched into a vessel containing 100 mL of methylene chloride and an excess of 4-fluorobenzoylmagnesium bromide while maintaining the temperature between 0°–10° C. The mixture is stirred for 30 minutes. About 100 mL of water is added and the biphase mixture is filtered through a pad of Celite. The organic phase is separated and reduced to about half its volume by vacuum distillation. The solution is restored to its original volume with acetone. This concentration/fill procedure is repeated twice more. The resulting acetone solution (about 300 mL) is warmed to about 50° C. and was treated with about 100 mL of water to precipitate the product. The suspension is cooled, and the product, 17β-(4-fluorobenzoyl)-androsta-3-bromo-3,5-diene, is isolated by filtration and dried.

(ii). 17β-(4-fluorobenzoyl)-androsta-3-cyano-3,5-diene

A stirred mixture of 17β-(4-fluorobenzoyl)-androsta-3-bromo-3,5-diene (50 grams), cuprous cyanide (11.0 grams) and dimethylformamide (200 mL) is heated to reflux for 3.5 hours. The reaction is cooled to 90°–100° C. and quenched with stirring into a solution of 100 mL of conc. aqueous ammonia and 200 mL of water. The reaction flask is rinsed out with 25 mL of dimethylformamide, which is also added to the quench solution. The resulting suspension is extracted twice with 200 mL portions of methylene chloride, and the organic extracts is filtered through a pad of celite. The organic phase is washed with three 200 mL portions of 50/50 v/v conc. aqueous ammonia/water, followed by two 200 mL portions of water. The organic phase is concentrated under vacuum to 150 mL and 250 mL of ethanol is added. The solution is again concentrated under vacuum to 150 mL, and 250 mL of ethanol is added. The solution is concentrated under vacuum to 300 mL, and 30 mL of water is added to induce crystallization. The resulting suspension is chilled for 2 hours at 0°–5° C. The solid product is collected by filtration and is dried at 65° C. under vacuum to afford 17β-(4-fluorobenzoyl)-androsta-3-cyano-3,5-diene.

(iii). 17β-(4-fluorobenzoyl)-androsta-3,5-diene-3-carboxylic acid

A mixture of 17β-(4-fluorobenzoyl)-androsta-3-cyano-3,5-diene (20.0 grams), 50% aqueous sodium hydroxide (80 mL), and ethanol (200 mL) is heated to reflux for 18 hours. The reaction suspension is cooled to 50° C. and is added to a stirred mixture of 6N hydrochloric acid (300 mL) and methylene chloride (200 mL). The final pH of the aqueous phase is 1.5–2.0. The organic phase is separated and the aqueous phase is reextracted with 250 mL of methylene chloride. The combined organic phases are stirred with 2 grams of decolorizing charcoal for one hour and are filtered through a pad of celite. The organic phase was concentrated under vacuum to 120 mL and 200 mL of ethyl acetate is added. The suspension is again concentrated under vacuum to 120 mL and 200 mL of ehtyl acetate is added. The resulting suspension is concentrated under vacuum to a final volume of 120 mL and is heated at reflux for 2 hours. The suspension is chilled at 0°–5° C. for two hours and filtered. The solid product is dried under vacuum at 65° C. to afford 17β-(4-fluorobenzoyl)-androsta-3,5-diene-3-carboxylic acid.

EXAMPLE 2—Corresponding to Scheme II

17β-(Phenethylcarbonyl)-androsta-3,5-diene-3-carboxylic Acid (i). 3-(trifluoromethanesulfonyloxy)-androst-3,5-diene-17β-carboxylic acid A solution of androst-4-en-3-one-17β-carboxylic acid (8.0 g; 25 mmol), 2,6-di-t-butyl-4-methyl pyridine (16.6 g; 62 mmol) and trifluoromethane sulfonic anhydride (11 ml; 66 mmol) in methylene chloride was stirred at 5° C. for 20 hours. The organic solvent was evaporated and the residue is dissolved in tetrahydrofuran water (99.5:0.5) with 4-dimethylaminopyridine (9.0 g) which upon acidification with hydrochloric acid followed by conventional workup yield 13 grams of the title compound (92% yield). MP 182° C.

(ii). S-(2-pyridyl)-3-(trifluoromethanesulfonyloxy)-androsta-3,5-diene-17β-thiocarboxylate A solution of 3-(trifluoromethanesulfonyloxy)-androsta-3,5-diene-17β-carboxylic acid (6.2 g; 14.9 mmol), triphenylphosphine (9.92 g; 38 mmol) and, 2,2'-dipyridyl disulfide (8.68 g; 39.5 mmol) in $CH_2CL_2$ (50 ml) was stirred under nitrogen for 20 hours. The reaction mixture was concentrated and the residue was passed directly through silica gel and appropriate fractions evaporated to yield 4.0 g of the title compound (50% yield). MP 120°–122° C.

(iii). 17β-(Phenethylcarbonyl)-androsta-3,5-diene-3-trifluoromethane sulfonate

To a solution of S-(2-pyridyl)-3-(trifluoromethanesulfonyloxy)-androsta-3,5-diene-17β-thiocarboxylate (0.3 g; 0.56 mmol) in tetrahydrofuran (20 ml) at about –50° C. was added phenethylmagnesium bromide (1.6 mmol). The reaction mixture was warmed to about –10° C., and diluted with a saturated aqueous ammonium chloride solution. Conventional workup with subsequent isolation by column chromatography yielded 166 mg of the title compound (60% yield). MP 98°–99° C.

(iv). 17β-(Phenethylcarbonyl)-androsta-3,5-diene-3-carboxylic acid

A mixture of 17β-(phenethylcarbonyl)-androsta-3,5-diene-3-trifluoromethane sulfonate (0.125 g; 0.23 mmol), potassium acetate (0.130 g; 1.32 mmol) and bis(triphenylphosphine) palladium (II) diacetate (0.015 g; 0.02 mmol) in DMF (3 ml) was purged with carbon monoxide for 2 minutes and stirred under a CO balloon at 60° C. for 2 hours. Reaction was diluted with water; acidified with 0.5 NHCl and extracted with ethylacetate and ethyl acetate extracts washed with water, dried (MgSO4) and evaporated under vacuum. The residue was chromatographed on a silica gel column eluting with hexane:ethylacetate:acetic acid 70:30:1. The solid obtained was recrystalized from acetonitrile to give 17 mg (17%) of white solid. MP 218°–220° C.

EXAMPLE 3—Corresponding to Scheme II

17β-(4-Fluorobenzoyl)-androsta-3,5-diene-3-carboxylic Acid

The title compound was prepared according to Example 2 (i–iv) by substituting 4-fluorobenzoylmagnesium bromide for phenethylmagnesium bromide in step iii. MP 255° C.

EXAMPLE 4—Corresponding to Scheme II

7β-(4-fluorobenzoyl)-androsta-3,5-diene-3-carboxylic Acid (i). 3-(fluorosulfonyloxy)-androsta-3,5-diene-17β-carboxylic acid A solution of androsta-4-en-3-one-17β-carboxylic acid, 2,6-di-t-butyl-4-methyl pyridine and fluorosulfonic anhydride in methylene chloride is stirred at 5° C. for 20 hours. The reaction mixture is washed with aqueous hydrochloric acid and water. The organic phase is concentrated and the resulting residue is purified by column chromatography to yield the title compound.

(ii). S-(2-pyridyl)-3-(fluorosulfonyloxy)-androsta-3,5-diene-17β-thiocarboxylate A solution of 3-(fluorosulfonyloxy)-androsta-3,5-diene-17β-carboxylic acid, triphenylphosphine and, 2,2'-dipyridyl disulfide in toluene is stirred under nitrogen for 20 hours. The reaction mixture is concentrated and the residue is passed directly through silica gel and appropriate fractions evaporated to yield title compound.

(iii). 17β-(4-fluorobenzoyl)-androsta-3,5-diene-3-fluorosulfonate

To a solution of S-(2-pyridyl)-8-(fluorosulfonyloxy)-androsta-3,5-diene-17β-thiocarboxylate in tetrahydrofuran at about –50° C. is added 4-fluorobenzoylmagnesium bromide. The reaction mixture is warmed to about –10° C. and diluted with a saturated aqueous ammonium chloride solution. Conventional workup with subsequent isolation by column chromatography yields title compound.

(iv). Methyl 17β-(4-fluorobenzoyl)-androsta-3,5-diene-3-carboxylate

A solution of 17β-(4-fluorobenzoyl)-androsta-3,5-diene-3-fluorosulfonate, triphenyl phosphine, palladium II acetate, triethylamine, methanol and dimethyl formamide is stirred vigorously under a carbon monoxide atmosphere for 20 hours. Conventional workup with subsequent isolation by column chromatography yields title compound.

(v). 17β-(4-fluorobenzoyl)-androsta-3,5-diene-3-carboxylic acid

A mixture of methyl 17β-(4-fluorobenzoyl)-androsta-3,5-diene-3-carboxylate, $K_2CO_3$, water and methanol is heated at reflux for about 5 hours. Acidification followed by conventional workup yields title compound.

EXAMPLE 5—Corresponding to Scheme II

17β-(4-fluorobenzoyl)-androsta-3,5-diene-3-carboxylic Acid (i). 3-(Fluorosulfonyloxy)-androsta-3,5-diene-17β-carboxylic acid The title compound is prepared according to Example 4(i).

(ii). 3-Cyano-androsta-3,5-diene-17β-carboxylic acid

A solution of 3-(fluorosulfonyloxy)-androsta-3,5-diene-17β-carboxylic acid in dimethylformamide is treated with an excess of cuprous cyanide at reflux. The reaction solution is quenched into aqueous Ammonia and is filtered. The filtered solids are dissolved in methyline chloride/aqueous hydrochloric acid. Conventional workup and isolation by column chromatography yields the title compound.

(iii). S-(2-pyridyl)-3-cyano-androsta-3,5-diene-17β-thiocarboxylate

The title compound is prepared according to Example 2(ii) by substituting 3-cyano-androsta-3,5-diene-17β-carboxylic acid, prepared as in Example 5(ii), for 3-(trifluoromethanesulfonyloxy)-androsta-3,5-diene-17β-carboxylic acid.

(iv). 3-cyano-17β-(4-fluorobenzoyl)-androsta-3,5-diene

The title compound is prepared according to Example 2(iii) by substituting S-(2-pyridyl)-3-cyano-androsta-3,5-diene-17β-thiocarboxylate, as prepared in Example 5(iii), for S-(2-pyridyl)-3-(trifluoromethanesulfonyloxy)- androsta-3,5-diene-17β-thiocarboxylate and by substituting 4-fluorobenzoylmagnesium bromide for phenylmagnesium bromide.

(v). 17β-(4-fluorobenzoyl)-androsta-3,5-diene-3-carboxylic acid

A mixture of 3-cyano-17β-(4-fluorobenzoyl)-androsta-3,5-diene excess sodium hydrochloride and ethanol is heated at reflux. The resulting mixture is quenched with aqueous hydrochloric acid, and is extracted with methylene chloride. Conventional workup and isolation by column chromatography yields the title compound.

EXAMPLE 6—Corresponding to Scheme III

17β-(4-fluorobenzoyl)-androsta-3,5-diene-3-carboxylic acid (i). methyl 17β-cyano-androsta-3,5-diene-3-carboxylate Phosophorus oxychloride is added to a solution of (17β)-17-N-t-butyl carboxamidyl androsta-3,5-diene-3-carboxylic acid in benzene (500 ml) and is heated to reflux. After 12 h the reaction is treated with MeOH (10 ml), then aqueous NaHCO₃, extracted with CH₂Cl₂, dried (MgSO4), filtered, concentrated, chromatographed and recrystallized to yield the title compound.

(ii). 17β-carboxaldehydo-androsta-3,5-diene-3-methanol

Diisobutyl aluminum hydride is added to a solution of methyl (17β)-17-cyano androsta-3,5-diene-3-carboxylate in toluene at RT. After 3.5 h, the reaction is quenched with aqueous H₂SO₄ and is stirred for 2 h. The organic layer is extracted with brine, H₂O, then is dried (MgSO4), filtered, concentrated, and chromatographed to yield the title compound.

(iii). 17β-(4-fluorobenzoyl)-androsta-3,5-diene-3-methanol 4-fluorobenzoylmagnesium bromide is added to a solution of (17β)-17-carboxaldehydo-androsta-3,5-diene-3-methanol in THF at 0 degrees C. After 0.5 h the reaction is quenched with aqueous ammonium chloride, the aqueous layer is extracted with EtOAc, the combined organic extracts are dried (MgSO₄), filtered, concentrated, and chromatographed to yield the title compound.

(iv). 17β-(4-fluorobenzoyl)-androsta-3,5-diene-3-carboxaldehyde

Tetrapropyl ammonium perruthenate is added to a solution of (17β)-17-(5,5,5-trifluoro-1-hydroxypentyl)-androsta-3,5-diene-3-methanol and 4-methylmorpholine N-oxide in CH₂Cl₂ (2.0 ml) at RT. After 1 h the reaction is flash chromatographed to yield the title compound.

(v). 17β-(4-fluorobenzoyl)-androsta-3,5-diene-3-carboxylic acid

Sodium chlorite is added to a mixture of 17β-(4-fluorobenzoyl)-androsta-3,5-diene-3-carboxaldehyde, sodium phosphate, monobasic monohydrate in 2-methyl-2-butene in THF, H₂O, and t-butanol at RT. After 6 h acetic acid was added, then the aqueous layer is extracted with EtOAc, the combined organic extracts are dried (MgSO₄), filtered, concentrated, and flash chromatographed to yield the title compound.

EXAMPLE 7—Corresponding to General Method A

17β-(4-fluorobenzoyl)-androsta-3,5-diene-3-carboxylic Acid

Into a 250 ml 3-neck round bottom flask is placed 17β-(4-fluorobenzoyl)-androsta-3,5-diene-3-carboxylic acid and an excess of sodium hydroxide. To the flask is added dimethyl sulfoxide as a solvent. The mixture is heated to reflux for 3 hours. Standard workup followed by isolation by preparative HPLC yields title compound.

EXAMPLE 8

An oral dosage form for administering Formula I comounds is produced by screening, mixing, and filling into hard gelatin capsules the ingredients in the proportions shown in Table 1, below.

TABLE I

| Ingredients | Amounts |
| --- | --- |
| 17β-(4-fluorobenzoyl)-androsta-3,5-diene-3-carboxylic acid | 50 mg |
| magnesium stearate | 5 mg |
| lactose | 75 mg |

EXAMPLE 9

The sucrose, calcium sulfate dihydrate and Formula (I) compound shown in Table II below, are mixed and granulated in the proportions shown with a 10% gelatin solution. The wet granules are screened, dried, mixed with the starch, talc and stearic acid, screened and compressed into a tablet.

TABLE II

| Ingredients | Amounts |
| --- | --- |
| 17β-(4-fluorobenzoyl)-androsta-3,5-diene-3-carboxylic acid | 100 mg |
| calcium sulfate dihydrate | 150 mg |
| sucrose | 20 mg |
| starch | 10 mg |
| talc | 5 mg |
| stearic acid | 3 mg |

EXAMPLE 10

17β-(4-fluorobenzoyl)-androsta-3,5-diene-3-carboxylic acid, 75 mg, is dispursed in 25 ml of normal saline to prepare an injectable preparation.

While the preferred embodiments of the invention are illustrated by the above, it is to be understood that the invention is not limited to the precise instructions herein disclosed and that the right to all modifications coming within the scope of the following claims is reserved.

What is claimed is:

1. A compound represented by the Formula

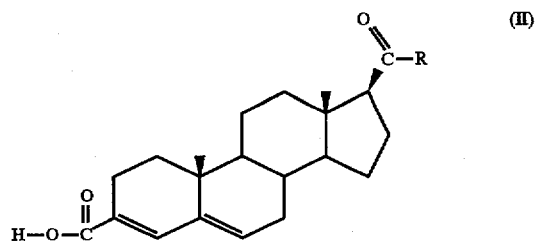

(II)

in which

R is a $C_6$-aryl substituted with one or more halogens and pharmaceutically acceptable salts, hydrates, solvates and esters thereof.

2. A compound of claim 1 that is

17β-(4-fluorobenzoyl)-androst-3,5-diene-3-carboxylic acid, and pharmaceutically acceptable salts, hydrates, solvates and esters thereof.

3. A pharmaceutical composition comprising a compound according to claim 1 and a pharmaceutically acceptable carrier.

4. A method of inhibiting steroid 5-α-reductase in mammals which comprises the administration to a mammal in need such inhibition, an effective amount of a compound claim 1.

* * * * *